United States Patent [19]

Seelich

[11] Patent Number: 4,816,251

[45] Date of Patent: Mar. 28, 1989

[54] METHOD OF INACTIVATING REPRODUCTIVE FILTERABLE PATHOGENS IN FIBRINOGEN AND FACTOR XIII COMPOSITIONS

[75] Inventor: Thomas Seelich, Vienna, Austria

[73] Assignee: Immuno Aktiengesellschaft fur chemisch-medizinische Produkte, Vienna, Austria

[21] Appl. No.: 775,609

[22] Filed: Sep. 13, 1985

[30] Foreign Application Priority Data

Sep. 28, 1984 [AT] Austria ................................ 3084/84

[51] Int. Cl.$^4$ .............................................. A61K 35/14
[52] U.S. Cl. ......................................... 424/101; 514/2; 514/8; 530/381; 530/382
[58] Field of Search ........................ 435/236; 424/101; 530/382, 383; 514/2, 8

[56] References Cited

U.S. PATENT DOCUMENTS

| | | | |
|---|---|---|---|
| 4,297,344 | 10/1981 | Schwinn et al. | 530/383 X |
| 4,362,567 | 12/1982 | Schwarz et al. | 424/101 X |
| 4,414,976 | 11/1983 | Schwartz et al. | 128/334 R |
| 4,456,590 | 6/1984 | Rubinstein | 424/101 |
| 4,640,834 | 2/1987 | Eibl et al. | 435/236 X |

FOREIGN PATENT DOCUMENTS

| | | |
|---|---|---|
| 142059 | 5/1985 | European Pat. Off. . |
| WO82/03871 | 11/1982 | PCT Int'l Appl. . |
| 0103196 | 3/1984 | United Kingdom . |

OTHER PUBLICATIONS

The Merch Index, 10th Ed., #7240.
Biochem. Biophys. Res. Comm. 56, 793–798, 1974; L. L. Shen et al.; "Fibrin Gel Structure; Influence of Calcium and Covalent Crosslinking on the . . . "
T. Seelich, H. Redl; "Theoretische Grundlagen des Fibrinklebers" and R. K. Schattauer Verlag, Stuttgart-N.Y., 199–208, 1980; K. Schimpf: Fibrinogen, Fibrin und Fibrinkleber.
Biomed. Res. 4, 155–160, 1983, S. Kasai, T. Kunimoto, K. Nitta–"Cross–Linking of Fibrin by Activated Factor XIII Stimulates Attachment, . . . ".
"MIR" Publishers, Moscow 1969, pp. 471–475; Rosenberg et al.–XII, International Congress on Blood Transfusion, Abstracts, USP XVI, p. 298–Fibrinogen.
*Fresenius' Z. Anal. Chem.* 314: pp. 567–571, E. Scholz–"Karl Fischer Reagents Without Pyridine (8), Coulometric Determination of Water".
J. Bio. Chem. 244: pp. 4406–4412, 1969, K. Weber et al.–"The Reliability of Molecular Weight Determinations by Dodecylsulfate–Polyacrylamide Gel . . . ".
Amer. J. Hyg., vol. 27: pp. 493–497, 1938, J. L. Reed et al., "A Simple Method of Estimating Fifty Per Cent Endpoints".

Primary Examiner—Sam Rosen
Attorney, Agent, or Firm—Burns, Doane, Swecker & Mathis

[57] ABSTRACT

There is disclosed a method of inactivating reproductive filterable pathogens in tissue adhesives containing fibrinogen and Factor XIII, with their biologic activity being largely preserved. In order to provide a tissue adhesive preparation of human or animal origin, which exhibits a high safety with respect to reproductive filterable pathogens and whose biologic activity is largely preserved, preparations having a minimum content of 100 units of Factor XIII/g of fibrinogen are heated in the dry state in the presence of an oxygen-free inert protective gas or under vacuum.

13 Claims, No Drawings

METHOD OF INACTIVATING REPRODUCTIVE FILTERABLE PATHOGENS IN FIBRINOGEN AND FACTOR XIII COMPOSITIONS

The invention relates to a method of inactivating reproductive filterable pathogens in tissue adhesives containing fibrinogen and Factor XIII, with their biologic activity being largely preserved.

Tissue adhesives are made of human or animal blood or plasma and serve to physiologically glue tissue or bone parts, seal wounds, stop bleedings and to promote wound healing. They contain, as active components, fibrinogen and Factor XIII and, if desired, may contain additional plasma proteins, such as, e.g., fibronectin, albumin, plasminogen activator inhibitors and/or plasma inhibitors, as well as further additives.

The mode of action of these tissue adhesives is based on the conversion of soluble fibrinogen into insoluble fibrin, upon the activation of Factor XIII to Factor XIIIa by thrombin in the presence of $Ca^{2+}$ ions and upon crosslinking of the formed fibrin by Factor XIIIa to a high polymer. The crosslinking of fibrin, in particular of the fibrin α-chains, is of a particular relevance, because the strength of the formed clot and, thus, of the adhesion, is considerably increased thereby (L. L. Shen, R. P. McDonagh, J. Hermanns jr.: "Fibringel Structure: Influence of Calcium and Covalent Crosslinking on the Elasticity". Biochem. Biophys. Res. Comm. 56, 793–798, 1974; T. Seelich, H. Redl: "Theoretische Grundlagen des Fibrinklebers" in: K. Schimpf: "Fibrinogen, Fibrin and Fibrinkleber", F. K. Schattauer Verlag, Stuttgart-New York, 199–208, 1980).

The quality of a tissue adhesive, therefore, substantially depends on its contents of soluble intact fibrinogen clottable with thrombin and on the ability of crosslinking of the formed fibrin by the Factor XIII present.

Despite careful tests of the starting products at the production of blood preparations, the risk of patients falling ill with microbial infections after a treatment is not low. To be sure, there have been various attempts to inactivate pathogens, yet the safety of the preparation is not always ensured, the biologic activity of active substances being impaired.

With preparations that are destined for infusion purposes, it is possible to compensate losses in the biologic activity by accordingly higher dosages, which affects the economy, yet not the efficacy of the products. With tissue adhesives, however, it is not possible to compensate for a reduced biologic activity (expressed by the content of intact soluble fibrinogen clottable with thrombin and by the ability of crosslinking of the thus formed fibrin) by a higher dosage. For, an adhesion will by no means become stronger by using more adhesive of lesser quality. Moreover, it is known that crosslinked fibrin stimulates the growth of fibroblasts and, thus, the healing of wounds, while fibrinogen or non-crosslinked fibrin hardly exhibit this desired effect (S. Kasai, T. Kunimoto, K. Nitta: "Cross-Linking of Fibrin by Activated Factor XIII Stimulates Attachment, Morphological Changes and Proliferation of Fibroblasts", Biomed. Res. 4, 155–160, 1983).

Hence follows the demand both that inactivation methods for tissue adhesive preparations must be highly effective with respect to reproductive filterable pathogens, such as viruses, and that the biologic activities of these preparations must be preserved to a major extent.

There are known various methods in which blood products are subjected to heat treatment in order to inactivate reproductive filterable pathogens contained therein.

Thus, in the published PCT application WO 82/03871, a method for treating blood clotting enzyme compositions is described, wherein the latter are heated in the dry state to inactivate infectious viruses present. By "dry state" a water content of up to 0.05 (5% by weight) is meant. The compositions mentioned there do, however, not contain fibrinogen and Factor XIII; they are not tissue adhesive preparations.

Rosenberg et al. in a treatise of the XIIth International Congress on Blood Transfusion, Abstracts, "MIR" Publishers, Moscow 1969, pp. 473–475, describe a method for inactivating albumin solutions and fibrinogen in the dry state by 10 hours of heating at 60° C. This intravenously administrable preparations were destined to treat fibrinogen deficiency syndromes, for which the fibrinogen had to be soluble and clottable. These preparations did not contain Factor XIII and were not destined for tissue gluing.

Furthermore, a method for the production of a tissue adhesive preparation is known from European patent application Ser. No. 103,196, in which a tissue adhesive solution is heated in the presence of calcium ions as well as of large amounts of sucrose and glycine as stabilizing agents during the fractionation process. However, that method has the disadvantage that large amounts of stabilizing agents must be added during heating and must be removed afterwards. Therein, part of the fibrinogen is denatured and must be separated after the heating stage. In addition, treatments of this kind have the disadvantage that the stabilizing agents added stabilize, with respect to heat, not only the proteins, but also the possibly present viruses. The efficiency of such methods, therefore, can by no means be compared to the efficiency of the standardized heat treatment of albumin solutions (10-hour heating at 60° C.), because the latter can be performed without the addition of major amounts of stabilizing agents due to the extraordinarily high heat resistance of the albumin molecule.

This invention aims at avoiding the disadvantages of the known inactivation methods and has as its object to provide a tissue adhesive preparation of human or animal origin, which exhibits a high safety with respect to reproductive filterable pathogens, such as viruses, and whose biologic activity is largely preserved, i.e., generally to a value greater than 70% as compared to the untreated tissue adhesive preparation, which means that the fibrinogen, in a high concentration, remains soluble and clottable with thrombin and the formed fibrin exhibits a high crosslinking ability. In particular, a sufficient strength of the gluing site and a rapid wound healing without complications are to be ensured upon wound treatment with the tissue adhesive prepared according to the invention.

To achieve this object, the method according to the invention consists in that tissue adhesive preparations having a minimum content of 100 units of Factor XIII/g of fibrinogen are heated in the dry state in the presence of an oxygen-free inert protective gas, preferably nitrogen, or under vacuum. By "dry state", a water content of up to 5% by weight is meant.

Suitably, heating may take place at a temperature in the range of 50° to 120° C. for a period of time of from at least 1 min to more than 100 h, the shortest period of heating corresponding to the highest temperature and vice versa. The heat treatment can be realized at any stage of the production process and/or after filling the preparation into final containers.

The "dry state" of the tissue adhesive preparation can be brought about and safeguarded by after-drying with water-binding agents, such as phosphorus pentoxide.

According to a preferred embodiment, a tissue adhesive preparation is produced by fractionation of human cryoprecipitate and further Factor XIII is added to the native content of Factor XIII, preferably until a total content of Factor XIII of about 500 units/g fibrinogen is obtained, the heat treatment being effected at any stage of the fractionation process and/or after filling the preparation into final containers.

The thermally treated preparation advantageously can be stored in final containers in the dry state and dissolved to a concentration of at least 70 mg of fibrinogen per ml, prior to its application.

It is, however, also possible to dissolve the product after the heating stage, fill it into final containers and store it in the deepfrozen state so as to remain stable.

The method according to the invention is based on new findings, namely:

(1) The stability (thermal load-bearing capacity) of the preparations during heat treatment is substantially higher under an oxygen-free protective gas or under vacuum than with the access of air.

(2) The stability (thermal load-bearing capacity) of tissue adhesive preparations increases with an increasing content of Factor XIII, yet decreases with an increasing content of water (residual moisture).

(3) The degree of inactivation of the heat treatment in the dry state under an oxygen-free atmosphere substantially is the same as under the access of air.

These facts are illustrated by way of the results from the following Experiments.

EXPERIMENT 1

Stability of tissue adhesive preparations with different water contents, under nitrogen or under vacuum, on the one hand, and under air, on the other hand.

A tissue adhesive preparation was prepared in a known manner according to the method described in U.S. Pat. No. 4,414,976: 277 l human fresh plasma frozen at $-20°$ C. were heated to $+2°$ C., the resulting cryoprecipitate was separated by centrifugation and treated with a buffer solution having a pH of 6.5 and containing 6.6 g $Na_3$ citrate.$2H_2O$, 3.4 g NaCl, 10.0 g glycine, 25,000 KIU aprotinin and 200 I.U. heparin per liter, and was centrifuged a second time at $+2°$ C. The separated precipitate was dissolved in a further buffer solution having a pH of 7.9 and containing 19.0 g human albumin, 9.0 g glycine, 1.0 g trisodium citrate.$2H_2O$, 25,000 KIU aprotinin and 200 I.U. heparin per liter, and was adjusted to a protein concentration of 50 g per liter. This solution was sterile filtered, filled into final containers (vials) of 12.5 ml each, deepfrozen and lyophilized. In the thus obtained preparation, the ratio of Factor XIII to fibrinogen, expressed in units Factor XIII per gram fribrinogen, amounted to 109; the water content (residual moisture) of the preparation was less than 0.01 (1% by weight).

The content of fibrinogen was determined according to the prescription of USP XVI, p. 298, as the protein clottable by thrombin determined according to the method of Kjeldahl.

The content of Factor XIII was determined by means of a fibrin crosslinking test, in which Factor XIII-free fibrinogen was used as the substrate, in the following manner:

0.5 ml of a Factor XIII-free fibrinogen solution, having a fibrinogen content of 10 mg/ml, are each mixed with 0.05 ml of different dilutions of the sample to be determined and 0.1 ml of a solution containing 60 I.U. thrombin and 130 $\mu$Mol $CaCl_2$ per ml, and are incubated at 37° C. After an incubation time of 2 hours, the reaction is stopped, and the disulfide bridges contained in the proteins are reductively split, by the addition of a mixture of urea, sodium dodecyl sulfate (SDS) and $\beta$-mercaptoethanol. The degree of crosslinking of the fibrin-$\gamma$-chains is densitometrically determined after SDS polyacrylamide gel electrophoresis (K. Weber, M. Osborn: "The Reliability of Molecular Weight Determinations by Dodecylsulfate-Polyacrylamide-Gel Electrophoresis". J. Biol. Chem. 244, 4406–4412, 1969) of the thus obtained samples and staining with Coomassie blue and serves as the measure for the Factor XIII content.

As standard, pooled human citrated plasma serves, wherein, by definition, 1 ml of plasma contains 1 unit of Factor XIII. Thos dilutions of the sample and of the standard which cause a 50% crosslinking of the fibrin $\gamma$-chains are determined and the factor XIII content of the original sample is calculated according to the formula $$X=(Vx)/(Vs)$$

wherein:

Vx is the dilution of the unknown sample, and
Vs is the dilution of the standard.

The water content was determined by extraction with anhydrous methanol according to the method of Karl Fischer, in a titrator according to the coulometric method (E. Scholz, Fresenius' Z. anal. Chem. 314, 567–571, 1983).

Part of the freeze-dried tissue adhesive preparation obtained in the manner described, was dissolved to a protein concentration of 50 mg/ml, filled into vials of 2.5 ml each, deepfrozen and freeze-dried anew.

Subsequently, samples were adjusted to have different water contents, viz 0.007 (0.7% by weight), 0.03 (3% by weight) and 0.05 (5% by weight), respectively. The samples with a water content of 0.007 were hermetically sealed either under vacuum ($<10$ Pa, i.e., $<0.1$ mbar) or under $N_2$ or under air at normal pressure. The samples with water contents of 0.03 and 0.05 were closed either under $N_2$ or under air.

Several samples of each kind were then heated to 60° C. for 10 hours and, afterwards, the residual activity, i.e., the content of intact fibrinogen clottable with thrombin and the crosslinking ability of the fibrin $\alpha$-chains were determined as the measure for the biologic activity, the lyophilized heated or non-heated samples having been dissolved with 1.0 ml of distilled water each.

The determination of the crosslinking ability of the fibrin $\alpha$-chains was effected by way of a crosslinking test (T. Seelich, H. Redl: "Theoretische Grundlagen des Fibrinklebers" in K. Schimpf: "Fibrinogen, Fibrin and Fibrinkleber", F. K. Schattauer Verlag, Stuttgart-New York, 199–208, 1980), in which, after mixing of the dissolved ready-for-use tissue adhesive with an equal volume of a solution containing 40 $\mu$Mol $CaCl_2$ and 15 I.U. thrombin per ml, the mixture is incubated at 37° C. After stopping of the reaction and reductive splitting of the disulfide bridges contained in the proteins by the addition of a mixture of urea, sodium dodecyl sulfate (SDS) and β-mercaptoethanol, the degree of crosslinking of the fibrin α-chains is densitometrically determined by means of SDS polyacrylamide gel electrophoresis (K. Weber, M. Osborn: "The Reliability of Molecular Weight Determinations by Dodecyl-Sulfate-Polyacrylamide Gel Electrophoresis", J. Biol. Chem. 244, 4406-4412, 1969) and staining with Coomassie blue.

The results obtained are summarized in Table 1.

A non-heated sample served as a reference for the samples heated under different conditions. A comparison of the values found for the crosslinking of fibrin α-chains clearly shows that firstly the stability of the tissue adhesive with heating under $N_2$ or under vacuum is considerably better than under air and secondly that the stability decreases with an increasing water content.

TABLE 1

Stability of a tissue adhesive with different water contents at heating at 60° C. under $N_2$, vacuum or air.

| Water content | Heating at 60° C. Hours | Atmoshere | Residual activity Fibrinogen (Clottable protein) (mg/ml) | Crosslinking of fibrin α-chains after 2 hours |
|---|---|---|---|---|
| 0.007 | 0 | $N_2$ | 85 | 0.80 |
| 0.007 | 10 | $N_2$ | 84 | 0.76 |
| 0.007 | 10 | vacuum | 84 | 0.74 |
| 0.007 | 10 | air | 80 | 0.59 |
| 0.03 | 10 | $N_2$ | 83 | 0.60 |
| 0.03 | 10 | air | 80 | 0.21 |
| 0.05 | 10 | $N_2$ | 84 | 0.24 |
| 0.05 | 10 | air | 79 | 0.11 |

EXPERIMENT 2

Stability of tissue adhesive preparations with different contents of Factor XIII, expressed by the ratio of units of Factor XIII per gram of fibrinogen:

A tissue adhesive preparation was produced in the same manner as in Experiment 1. Part thereof was dissolved to a protein concentration of 50 mg/ml; the solution was divided into two parts.

To one part 15 units of Factor XIII per ml were admixed. Both parts were then filled into a number of vials in portions of 2.5 ml each, deepfrozen, lyophilized and closed under $N_2$. The contents of fibrinogen and Factor XIII were determined as described in Experiment 1 and the content of Factor XIII per gram of fibrinogen was calculated for each of the two preparations.

Several samples of the two preparations were heated at 60° C. and 80° C. for differently long periods of time. Two samples each were taken prior to heating and at predetermined points of time during the heating process, respectively, to measure the residual activity.

The determination of the residual activity was effected as described in Experiment 1. The results are summarized in Table 2.

A comparison of the values found for the crosslinking of the fibrin α-chains clearly shows that the stability of tissue adhesive preparations increases with an increasing content of Factor XIII, expressed as the ratio units of Factor XIII:grams fibrinogen.

TABLE 2

Stability of tissue adhesive preparations in dependence on the ratio Factor XIII: fibrinogen at heating

| Factor XIII: Fibrinogen (U/g) | Heating Hours | °C. | Residual activity Fibrinogen (Clottable protein) (mg/ml) | Crosslinking of fibrin α-chains after 2 hours |
|---|---|---|---|---|
| 109 | 0 | — | 85 | 0.81 |
| 109 | 30 | 60 | 83 | 0.57 |
| 109 | 100 | 60 | 84 | 0.50 |
| 109 | 10 | 80 | 85 | 0.67 |
| 109 | 30 | 80 | 84 | 0.48 |
| 489 | 0 | — | 83 | 0.95 |
| 489 | 30 | 60 | 84 | 0.87 |
| 489 | 100 | 60 | 83 | 0.85 |
| 489 | 10 | 80 | 82 | 0.79 |
| 489 | 30 | 80 | 84 | 0.75 |
| 489 | 100 | 80 | 84 | 0.69 |

EXPERIMENT 3

Stability of tissue adhesive preparations with a Factor XIII content of about 500 units per gram of fibrinogen and a water content of 0.005 at heating under $N_2$ at temperatures of up to 120° C.:

The production of the tissue adhesive preparation was effected in the same manner as in Experiments 1 and 2. The water content of the preparation was determined to be 0.005 and the ratio units Factor XIII:gram fibrinogen was determined to be 496. Samples of the preparations were heated to different temperatures in the range between 60° C. and 120° C. for different periods of time. Two samples each were taken prior to heating and after predetermined heating periods, respectively, to measure the residual activity. The determination of the residual activity was performed as described in Experiment 1.

The results are summarized in Table 3.

Considering the quality characteristics to be required for tissue adhesives based on fibrinogen and Factor XIII, i.e., a minimum content of fibrinogen of 70 mg/ml and a crosslinking of the fibrin α-chains in the described crosslinking test of at least 0.35 (35%), it follows that such tissue adhesive preparations, under the conditions indicated, can be heated for a considerably longer period of time than in this Experiment, without having to put up with too big quality losses.

TABLE 3

Stability of tissue adhesive preparations with a Factor XIII content of 496 units per gram of fibrinogen and a water content of 0.005 at heating under $N_2$

| Heating Hours | °C. | Residual activity Fibrinogen (Clottable protein) (mg/ml) | Fibrin α-chain crosslinking after 2 hours |
|---|---|---|---|
| 0 | — | 86 | 0.95 |
| 10 | 60 | 83 | 0.90 |
| 30 | 60 | 84 | 0.87 |
| 100 | 60 | 84 | 0.83 |
| 10 | 80 | 85 | 0.80 |
| 30 | 80 | 85 | 0.77 |
| 100 | 80 | 83 | 0.70 |
| 3 | 90 | 84 | 0.90 |
| 1 | 100 | 83 | 0.81 |
| 0.3 | 110 | 84 | 0.85 |
| 0.1 | 120 | 84 | 0.81 |

The method according to the invention including the inactivation of reproductive pathogens will be explained in more detail in the following examples. Since the necessary studies on virus inactivation in blood products cannot be carried out immediately in man, the assessment of the efficacy of inactivation is effected by way of model viruses.

EXAMPLE 1

Inactivation of a model virus (Sindbis virus) and residual activity of a tissue adhesive preparation at dry heating under $N_2$ or under vacuum, on the one hand, and under air, on the other hand:

The determination of the residual activity was performed as described in Experiment 1. The results are summarized in Table 4. They not only indicate that it is possible to completely inactivate Sindbis virus in tissue adhesive preparations of the defined kind, but also led to the important finding that the ratio between virus inactivation and residual activity of the preparation may be substantially improved by heating under the exclusion of oxygen, i.e., under an inert protective gas or under vacuum.

TABLE 4

Inactivation of a model virus (Sindbis virus) in a tissue adhesive preparation by dry heating under $N_2$, vacuum or air

| Heating at 60° C. | | Sindbis-virus titer ($\log_{10}$ TCID$_{50}$) | Residual activity | |
|---|---|---|---|---|
| Hours | Atmosphere | | Fibrinogen (Clottable protein) (mg/ml) | Crosslinking of fibrin α-chains after 2 hours |
| 0 | $N_2$ | 4.9 | 83 | 0.78 |
| 3 | $N_2$ | 4.2 | 85 | 0.65 |
| 10 | $N_2$ | 3.0 | 82 | 0.62 |
| 30 | $N_2$ | <1 | 84 | 0.58 |
| 0 | vacuum | 5.0 | 83 | 0.78 |
| 3 | vacuum | 4.2 | 83 | 0.67 |
| 10 | vacuum | 2.9 | 84 | 0.60 |
| 30 | vacuum | <1 | 85 | 0.57 |
| 0 | air | 5.0 | 83 | 0.78 |
| 3 | air | 4.0 | 82 | 0.60 |
| 10 | air | 2.9 | 82 | 0.51 |
| 30 | air | 1.5 | 81 | 0.39 |

A tissue adhesive preparation was produced in the same manner as in Experiment 1.

Part of the lyophilized tissue adhesive preparation obtained was dissolved to a protein concentration of 50 mg/ml, was admixed with a Sindbis virus suspension in cell culture medium TCM 199 or with virus-free cell culture medium, was filled into vials in portions of 2.6 ml each, deepfrozen and lyophilized to a water content of 0.005 (0.5% by weight). One part of the samples was hermetically sealed under vacuum (<10 Pa), another part under $N_2$ and a further part under air at normal pressure.

The closed samples were heated at a temperature of 60° C. for differently long periods of time. Three samples each were taken prior to heating and at predetermined points of time during the heating process to measure the virus titer, on the one hand, and the residual activity, on the other hand.

The determination of the virus titer was effected in the following manner: The samples were dissolved in 1.0 ml water each and were serially diluted with isotonic saline solution at a ratio of 1:10. The titer of the Sindbis virus was determined by assessment of the cytopathic effect on sensitive Vero cells in the microtiter plate. The results were expressed as logarithms TCID$_{50}$ after statistic processing of the evaluation according to the formula of Reed and Muench (J. L. Reed, H. Muench; Amer. J. Hyg. 27, 493, 1938).

EXAMPLE 2

The mode of operation of Example 1 was repeated, the difference being that after lyophilization, the samples were further dried ("after-dried") in the presence of a $P_2O_5$-containing desiccant under vacuum to a water content of 0.002, were closed under vacuum (<10 Pa) and were heated to 70° C. for different periods of time.

The results obtained are summarized in Table 5.

TABLE 5

Inactivation of a model virus (Sindbis virus) in a tissue adhesive preparation with a water content of 0.002 at heating at 70° C. under vacuum

| Heating Hours 70° C. | Sindbis-virus titer ($\log_{10}$ TCID$_{50}$) | Residual activity | |
|---|---|---|---|
| | | Fibrinogen (Clottable protein) (mg/ml) | Crosslinking of fibrin α-chains after 2 hours |
| 0 | 4.0 | 81 | 0.79 |
| 1 | 3.1 | 80 | 0.74 |
| 3 | 1.6 | 81 | 0.67 |
| 10 | <1 | 82 | 0.55 |

EXAMPLE 3

Inactivation of three different model viruses in a tissue adhesive preparation by dry heating at 60° C. under $N_2$:

A tissue adhesive preparation was produced as described in Experiment 1, and 12 units of Factor XIII per ml were added to the diluted solution of the tissue adhesive prior to sterile filtration. After lyophilization, the preparation contained 520 units of Factor XIII per gram of fibrinogen.

Part of the preparation obtained was dissolved to a concentration of 50 mg protein per ml, and one part of the solution was each admixed with a suspension of Sindbis virus or with a suspension of VSV (vesicular stomatitis virus) or with a suspension of LCM (lymphotropic choriomeningitis) virus in cell culture medium TCM 199, or with virus-free cell culture medium, was filled into vials in portions of 2.6 ml each, deepfrozen, lyophilized to a water content of 0.006 and closed under $N_2$. Samples of the preparations were heated to 60° C. and, as described in Example 1, the virus titer and the residual activity were determined prior to heating and after predetermined heating times.

The results are summarized in Table 6.

The outcome of Example 1, i.e., that Sindbis virus in a tissue adhesive preparation can be completely inactivated by 30 hours of dry heating at 60° C., was proved anew by this example. LCM virus and VSV had been completely inactivated already after 10 hours of heating.

The activity of the tissue adhesive preparation was almost completely preserved after 30 hours of heating.

TABLE 6

Inactivation of three different model viruses in a tissue adhesive preparation with a Factor XIII content of 520 units per gram fibrinogen and a water content of 0.006 at heating at 60° C. under $N_2$

| Heating Hours 60° C. | Virus titer ($\log_{10}$ TCID$_{50}$) | | | Residual activity | |
|---|---|---|---|---|---|
| | Sindbis | LCM | VSV | Fibrinogen (Clottable protein) (mg/ml) | Crosslinking of fibrin α-chains after 2 hours |
| 0 | 5.7 | 3.0 | 3.2 | 83 | 0.93 |
| 1 | | | 2.7 | | |
| 3 | 4.4 | 1.6 | 1.7 | | |
| 10 | 2.4 | <1 | <1 | | |
| 30 | <1 | <1 | <1 | 84 | 0.85 |

EXAMPLE 4

Inactivation of the bacteriophage X 174 at dry heating of a tissue adhesive preparation at 90° C.

A tissue adhesive preparation was produced as described in Example 3.

Part of the preparation obtained was dissolved to a protein concentration of 50 mg/ml and the solution was admixed with a suspension of the bacteriophage X 174 in culture medium for *Escherichio coli* 11303 or with virus-free culture medium filled in vials of 2.6 ml each, deepfrozen, lyophilized to a water content of 0.005 and closed under $N_2$.

A part of the samples was heated to 90° C. for different periods of time, and the virus titer and the residual activity were determined prior to heating and at predetermined times during the heating process.

The determination of the virus titer was effected in the following manner: The samples were dissolved in 1.0 ml $H_2O$ each and were serially diluted with 1 mM $MgCl_2$ at a ratio of 1:10. A mixture of 3 ml of 0.7% Bacto-Agar, 43° to 45° C., 100 μl of a suspension of *E. coli* in liquid medium and 200 μl of the bacteriophage containing sample or dilution were mixed and quickly poured on a nutritive agar plate (ATCC 129). After incubation over night at 37° C., the plaques formed by reproductive virus particles were counted in confluent cell layers by means of a counting device (PFU, plaque-forming units). The results were expressed as $\log_{10}$ PFU.

The determination of the residual activity was effected as described in Experiment 1. The results are summarized in Table 7. They indicate that the (relatively heat-resistant) bacteriophage X 174 can be completely inactivated in a tissue adhesive preparation by dry heating at 90° C. under $N_2$, the activity of the tissue adhesive preparation being preserved almost completely.

TABLE 7

Inactivation of a model virus (bacteriophage X 174) in a tissue adhesive preparation with a Factor XIII content of 520 units per gram fibrinogen and a water content of 0.005 at heating at 90° C. under $N_2$

| Heating Hours 90° C. | Bacteriophages X 174-virus titer ($\log_{10}$ PFU) | Residual activity | |
|---|---|---|---|
| | | Fibrinogen (Clottable protein) (mg/ml) | Crosslinking of fibrin α-chains after 2 hours |
| 0 | 5.8 | 82 | 0.95 |
| 0.3 | 4.1 | | |
| 1 | 1.9 | | |
| 3 | 0 | 83 | 0.90 |

EXAMPLE 5

Inactivation of Sindbis virus and canine hepatitis virus in a tissue adhesive preparation by dry heating at 110° C.

A tissue adhesive preparation was produced as described in Example 3.

Part of the freeze-dried tissue adhesive preparation obtained was dissolved to a protein concentration of 50 mg/ml, admixed with a Sindbis virus suspension or a canine hepatitis virus suspension in cell culture medium TCM 199 or with a virus-free cell culture medium, filled into vials of 2.6 ml each, deepfrozen, freeze-dried to a water content of 0.005 and closed under $N_2$. The samples were heated at a temperature of 110° C. for different periods of time and the activity of the preparation and the virus titer were determined, as described, prior to heating and at predetermined times during the heating process.

The results are summarized in Table 8.

This Example indicates that not only Sindbis virus, but also canine hepatitis virus, which is known to be particularly heat-resistant, in a tissue adhesive preparation can be completely inactivated according to the method of the invention without having to put up with too big losses of the biologic activity of the preparation.

TABLE 8

Inactivation of two model viruses (Sindbis virus and canine hepatitis virus) in a tissue adhesive preparation with a Factor XIII content of 520 units per gram fibrinogen and a water content Of 0.005 at heating at 110° C. under $N_2$

| Heating Minutes 110° C. | Virus titer ($\log_{10}$ TCID$_{50}$) | | Residual activity | |
|---|---|---|---|---|
| | Sindbis | Canine hepatitis | Fibrinogen (Clottable protein) (mg/ml) | Crosslinking of fibrin α-chains after 2 hours |
| 0 | 3.6 | 3.4 | 84 | 0.92 |
| 2 | 2.0 | 1.9 | | |
| 6 | 1.2 | 1.6 | | |
| 20 | <1 | <1 | | 0.85 |

TABLE 8-continued

Inactivation of two model viruses (Sindbis virus and canine hepatitis virus) in a tissue adhesive preparation with a Factor XIII content of 520 units per gram fibrinogen and a water content 0f 0.005 at heating at 110° C. under $N_2$

| Heating Minutes 110° C. | Virus titer ($log_{10}$ TCID$_{50}$) | | Residual activity | |
|---|---|---|---|---|
| | Sindbis | Canine hepatitis | Fibrinogen (Clottable protein) (mg/ml) | Crosslinking of fibrin α-chains after 2 hours |
| 60 | <1 | <1 | 83 | 0.78 |

EXAMPLE 6

Inactivation of three different model viruses (Sindbis virus, VSV and corona virus) in a tissue adhesive preparation having a water content of 0.04 at heating at 60° C. under $N_2$.

A tissue adhesive preparation was produced as described in Example 3.

Part of the freeze-dried tissue adhesive preparation obtained was dissolved to a protein concentration of 50 mg/ml and admixed with a suspension of Sindbis virus or a suspension of VSV (vesicular stomatitis virus) or a suspension of corona virus in cell culture medium TCM 199, or with virus-free cell culture medium, filled into vials in portions of 2.6 ml each, deepfrozen, lyophilized, adjusted to a water content of 0.04 and closed under $N_2$.

Samples of the preparation were heated at 60° C., and the residual activity and the virus titer were determined prior to heating and after predetermined heating times, as described in Example 1.

The results are summarized in Table 9.

Under the conditions indicated, a complete inactivation of Sindbis virus had been achieved after a heating period of only 3 hours, of VSV and of corona virus even after 1 hour, the activity of the preparation having been largely preserved.

TABLE 9

Inactivation of three different model viruses in a tissue adhesive preparation with a Factor XIII content of 520 units per gram fibrinogen and a water content of 0.04 at heating at 60° C. under $N_2$

| Heating Hours 60° C. | Virus titer ($log_{10}$ TCID$_{50}$) | | | Residual activity | |
|---|---|---|---|---|---|
| | Sindbis | VSV | corona | Fibrinogen (Clottable protein) (mg/ml) | Crosslinking of fibrin α-chains after 2 hours |
| 0 | 4.1 | 3.9 | 2.8 | 82 | 0.95 |
| 1 | 3.6 | <1 | 2.1 | | 0.85 |
| 3 | <1 | <1 | <1 | | 0.82 |
| 10 | <1 | <1 | <1 | 81 | 0.77 |

As previously discussed, the quality of a tissue adhesive substantially depends on (1) its contents of soluble intact fibrinogen clottable with thrombin and (2) on the ability of cross-linking of the formed fibrin by the Factor XIII present. Thus, the biological activity which is largely preserved relates to the above two factors. As indicated in Table IV, the cross-linking of fibrin alpha-chains after two hours is 0.78 when there is no heat treatment. After heating under a vacuum for 30 hours at 60° C., the cross-linking of fibrin alpha-chains after two hours is shown to be 0.57. Thus, 0.57/0.78 or 73% of the biological activity is retained. This is the lowest value reported in Table IV. Thus, in the other Examples, the biological activity has been retained to an even higher extent, i.e., more than 80%. The same conclusions can be drawn from Table 5 wherein the lowest cross-linking value amounts to 69.6% and wherein the other values amount to more than 80 or 90% of the initial value.

Thus, a tissue adhesive preparation containing fibrinogen and Factor XIII, with its biologic activity being largely preserved, means generally that the contents of soluble intact fibrinogen clottable with thrombin and the ability of cross-linking of the formed fibrin by the Factor XIII present are preserved to a value of greater than about 70%.

What I claim is:

1. A method of inactivating viruses and bacteriophages in a tissue adhesive preparation containing fibrinogen and Factor XIII, with its biologic activity being largely preserved, which method comprises heating a tissue adhesive preparation having a minimum content of 100 units of Factor XIII/g of fibrinogen in the presence of up to 5% by weight of water and in the presence of an oxygen-free inert protective gas or under vacuum, the heating being carried out at a temperature and for a sufficient period of time to inactivate the virus while largely preserving the biologic activity of the preparation.

2. A method as set forth in claim 1, wherein said protective gas is nitrogen.

3. A method as set forth in claim 1, wherein said heating of said tissue adhesive preparation is effected at a temperature of between 50° and 120° C. for a period of time of at least 1 min.

4. A method as set forth in claim 1, wherein said dry state of said tissue adhesive preparation is brought about by after-drying with a water-binding agent.

5. A method as set forth in claim 4, wherein said water-binding agent is phosphorus pentoxide.

6. A method as set forth in claim 1 wherein the heating is carried out at a temperature in the range of 50° to 120° C. for a period of time of from at least 1 min. to more than 10 hr.

7. A method of inactivating reproductive filterable pathogens in a tissue adhesive preparation containing fibrinogen and Factor XIII, with its biologic activity being largely preserved, which method comprises
producing said tissue adhesive preparation having a native content of Factor XIII by fractionation of human cryoprecipitate,
adding additional Factor XIII to said native content of Factor XIII,
drying said tissue adhesive preparation, and
heating said tissue adhesive preparation in the dry state in the presence of an oxygen-free inert protective gas or under vacuum, the heating being carried out at a temperature and a sufficient period of time to inactivate the virus while largely preserving the biologic activity of the preparation.

8. A method as set forth in claim 7, further comprising filling said preparation into final containers, and wherein said heating is effected after filling said preparation into said final containers.

9. A method as set forth in claim 8, wherein said heating is effected in any stage of said fractionation and after filling said preparation into said final containers.

10. A method as set forth in claim 7, wherein said adding of further Factor XIII is effected until a total content of Factor XIII of about 500 units/g of fibrinogen is reached.

11. A method as set forth in claim 8, wherein said adding of further Factor XIII is effected until a total content of Factor XIII of about 500 units/g of fibrinogen is reached.

12. A method as set forth in claim 9, wherein said adding of further Factor XIII is effected until a total content of Factor XIII of about 500 units/g of fibrinogen is reached.

13. A method as set forth in claim 7, wherein the heating is carried out at a temperature in the range of 50° to 120° C. for a period of time of from at least 1 min. to more than 10 hr.

* * * * *